(12) United States Patent
Purvis

(10) Patent No.: US 12,357,500 B2
(45) Date of Patent: Jul. 15, 2025

(54) MANDIBULAR ADVANCEMENT KIT AND DEVICE

(71) Applicant: Greystone IP Ltd, Coleraine (GB)

(72) Inventor: William Purvis, Coleraine (GB)

(73) Assignee: Greystone IP Ltd, Coleraine (GB)

( * ) Notice: Subject to any disclaimer, the term of this patent is extended or adjusted under 35 U.S.C. 154(b) by 308 days.

(21) Appl. No.: 17/792,199

(22) PCT Filed: Jan. 18, 2021

(86) PCT No.: PCT/EP2021/025019
§ 371 (c)(1),
(2) Date: Jul. 12, 2022

(87) PCT Pub. No.: WO2021/144150
PCT Pub. Date: Jul. 22, 2021

(65) Prior Publication Data
US 2023/0031988 A1    Feb. 2, 2023

(30) Foreign Application Priority Data

Jan. 17, 2020 (GB) ..................................... 2000710

(51) Int. Cl.
*A61F 5/56* (2006.01)
*A63B 71/08* (2006.01)

(52) U.S. Cl.
CPC ............ *A61F 5/566* (2013.01); *A63B 71/085* (2013.01)

(58) Field of Classification Search
CPC ........ A61F 5/05891; A61F 5/56; A61F 5/566; A61F 2005/563; Y10S 602/902;
(Continued)

(56) References Cited

U.S. PATENT DOCUMENTS 5,683,244 A * 11/1997 Truax ....................... A61C 7/36
433/24
11,278,444 B2   3/2022 Panthera
(Continued)

FOREIGN PATENT DOCUMENTS

WO    2018064772 A1    4/2018

OTHER PUBLICATIONS

International Search Report and Written Opinion dated May 13, 2021 for corresponding PCT/EP2021/025019 (12 pp).

*Primary Examiner* — Alireza Nia
*Assistant Examiner* — Gina McCarthy
(74) *Attorney, Agent, or Firm* — Renner, Kenner; Arthur M. Reginelli

(57) ABSTRACT

A mandibular advance advancement device generally indicated by the numeral 1. The mandibular advancement device 1 having a first member 2 and a second member 3. The first member 2 is configured to fit substantially over a portion of the teeth of the upper jaw of a user and the second member 3 is configured to fit substantially over a portion of the teeth of the lower jaw of the user. The mandibular advancement device 1 further has an engagement arrangement 4, configured to be engagable upon a forward manipulation of the lower jaw by the user, to maintain the lower jaw of the user in a predetermined protruding position relative to the upper jaw of the user and the natural biting position of the lower jaw.

28 Claims, 6 Drawing Sheets

(58) Field of Classification Search
CPC .. A61C 7/08; A61C 7/36; A61C 19/06; A61B 71/085
See application file for complete search history.

(56) References Cited

U.S. PATENT DOCUMENTS

| | | | |
|---|---|---|---|
| 2007/0283967 A1* | 12/2007 | Bailey | A61F 5/566 128/848 |
| 2011/0005526 A1* | 1/2011 | Garabadian | A61F 5/566 128/848 |
| 2014/0072927 A1* | 3/2014 | Diaz | A61C 7/08 433/6 |
| 2017/0035533 A1* | 2/2017 | Ross | A61C 9/0046 |
| 2018/0250100 A1* | 9/2018 | Ross | A61C 7/08 |
| 2019/0015246 A1* | 1/2019 | Kim | A61F 5/566 |
| 2020/0000626 A1 | 1/2020 | Farrell et al. | |

* cited by examiner

MANDIBULAR ADVANCEMENT KIT AND DEVICE

The present invention relates to a mandibular advancement device which is insertable in, and removeable from, the mouth by the user. In particular, to a mandibular advancement device for the treatment and prevention of snoring, sleep apnoea and similar disorders.

The present invention further relates to a mandibular advancement device for use by athletes participating in sport. In particular to a mandibular advance device in the form of a mouthguard to improve airflow to optimise the athletes breathing during sports.

Muscular relaxation in the throat area can occur in humans during sleep. This reduction in muscle tone causes a narrowing of the individual's pharynx. In some individuals, this narrowing of the pharynx can cause snoring. Snoring is a common problem and is caused by turbulence inside the airway during inspiration. In certain cases, snoring is often a manifestation of sleep apnoea whereby due to the narrowing of the pharynx, respiration is temporarily suspended for a certain period of time. This suspension of respiration causes the individual to awaken from sleep and is often repeated which can affect the quality of sleep; thus, effecting a person's day to day life and performance.

There are numerous devices to prevent snoring and sleep apnoea many of which operate by holding an individual's jaw forward and slightly ajar during sleep. As a result of this positioning, the muscles are stretched and strengthened minimising the narrowing of the pharynx due to muscular relaxation. This in turn reduces turbulence within the airway. By keeping the jaw slightly ajar airflow is also improved through the lips and mouth. Nonetheless, conventional mandibular advancement devices have several drawbacks.

First, these conventional devices tend to be bulky and because they hold the jaw permanently and rigidly in place. As a result, users tend to be intolerant of them due to their uncomfortable restrictiveness.

Secondly, conventional devices tend to be required to be removed from the mouth, adjusted and then reinserted. This method of adjustment can be disruptive, cumbersome and time-consuming especially considering the very nature of the device worn while the user is sleeping.

Thirdly, other conventional devices such as those noted in WO2014/043008 utilise hardware components such as expansion screws mounted upon a buccal surface in order to facilitate and control the positional adjustment of the lower jaw. This mechanical adjustment method again being cumbersome and time-consuming.

Finally, in conventional devices which utilise hardware components, such as expansion screws and straps in order to facilitate and control the positional adjustment of the lower jaw, it is becoming increasingly known that the area of the device where these hardware components attach is prone to fracture. Upon fracture replacement devices are required.

In sports, a mouthguard (commonly also referred to as a gumshield or mouth protector) is a device worn in the mouth of the athlete which is intended to protect the teeth, gums and jaw of the user. These conventional devices are adapted to fit over the teeth and a substantial portion of the gums of the upper jaw. However, conventional devices tend to be bulky and the natural position which provides the most comfort to users tends to be the natural biting position of the jaw. This results in muscular relaxation of the throat area, causing a narrowing of the athlete's pharynx which can cause turbulent airflow inside the airway during inspiration. This turbulent airflow reduces the flow rate of air inside the airway; thus, the breathing efficiency of the athlete is reduced.

It is an object of the present invention to obviate or mitigate one or more problems associated with the prior art and provide a more efficient mandibular advancement device with an increased ease of use.

It is a further object of the present invention to provide a mandibular advance device kit with increased ease of adjustment and readjustment.

It is a further object of the present invention to provide a mandibular advancement device for use in sports to improve air flow for an athlete.

Accordingly, the present invention provides a mandibular advancement kit comprising:
 a plurality of first members and at least one second member or at least one first member and a plurality of second members, and
 an engagement arrangement, configured to be engageable between a first member and a second member, to maintain the lower jaw of the user in a predetermined protruding position relative to the upper jaw of the user and the natural biting position of the lower jaw,
 wherein each first member and/or second member of the respective plurality are interchangeable with another from said plurality to advance the user's lower jaw at predetermined increments.

Preferably, the first member(s) configured to fit substantially over a portion of the teeth of the upper jaw of a user.

Ideally, the second member(s) configured to fit substantially over a portion of the teeth of the lower jaw of the user.

Preferably, the kit comprises at least one first member and/or at least one second member wherein the user's lower jaw is displaced by predetermined increments as the members are interchanged.

Preferably, the kit comprising multiple first members wherein each first member is mutually interchangeable with one another.

Ideally, the kit comprising multiple second members wherein each second member is mutually interchangeable with one another.

Preferably, the kit comprising multiple first members wherein each first member is mutually interchangeable with one another for being engageable to the second member.

Ideally, the kit comprising multiple second members wherein each second member is mutually interchangeable with one another for being engageable to the first member.

Advantageously, having a mandibular advancement kit having interchangeable first members and/or second members enables the user to enjoy varying degrees of advancement with a comfortable adjustment method beyond that of conventional mandibular advancement devices which require physical means of adjustment and readjustment typically by means of screws and straps.

Further advantageously, conventional mandibular advancement devices which require physical means of adjustment and readjustment are prone to fracturing at the point of attachment between the device and means of adjustment/readjustment, having interchangeable components negates and obliviates this risk of fracture.

Ideally, the user's lower jaw is displaced by predetermined increment of 0.01 mm.

Preferably, the user's lower jaw is displaced by predetermined increment of at least 0.01 mm.

Ideally, the user's lower jaw is displaced by predetermined increment of at least 0.02 mm.

Ideally, the user's lower jaw is displaced by predetermined increment of at least 0.05 mm.

Ideally, the user's lower jaw is displaced by predetermined increment of at least 0.075 mm.

Ideally, the user's lower jaw is displaced by predetermined increment of at least 0.1 mm.

Ideally, the user's lower jaw is displaced by predetermined increment of at least 0.15 mm.

Ideally, the user's lower jaw is displaced by predetermined increment of at least 0.2 mm.

Ideally, the user's lower jaw is displaced by predetermined increment of less than and/or equal to 50 mm.

Ideally, the user's lower jaw is displaced by predetermined increment of greater than 50 mm.

Ideally, the user's lower jaw is displaced by predetermined increment of less than and/or equal to 40 mm.

Ideally, the user's lower jaw is displaced by predetermined increment of less than and/or equal to 30 mm.

Ideally, the user's lower jaw is displaced by predetermined increment of less than and/or equal to 20 mm.

Ideally, the user's lower jaw is displaced by predetermined increment of less than and/or equal to 10 mm.

Ideally, the user's lower jaw is displaced by predetermined increments in the range of 0.2 mm to 10 mm.

Preferably, the user's lower jaw is displaced by predetermined increments in the range of 0.25 mm to 7.5 mm.

Ideally, the user's lower jaw is displaced by predetermined increments in the range of 0.3 mm to 6.5 mm.

Preferably, the user's lower jaw is displaced by predetermined increments in the range of 0.4 mm to 0.6 mm.

Preferably, the kit comprising multiple first members wherein each first member comprises first member engagement means located at different positions proximal to the anterior portion of the respective first member.

Ideally, the first member engagement means engages a second member engagement means on the second member.

Ideally, the kit comprising multiple second members wherein each second member comprises second member engagement means located at different positions proximal to the anterior portion of the respective second member.

Ideally, the second member engagement means engages a first member engagement means on the first member.

Preferably, the kit comprising multiple first members wherein each first member comprises first member engagement means extending longitudinally to varying lengths.

Ideally, the kit comprising multiple second members wherein each second member comprises second member engagement means extending longitudinally to varying lengths.

Advantageously, having varying positions and/or varying lengths of first member engagement means and/or second member engagement means provides the user with a mandibular advancement device with a comfortable and stepped adjustment/readjustment method which is bespoke to the individual user without cumbersome and time-consuming adjustments of conventional mandibular advancement devices.

A method for adaptively controlling a mandibular advancement device wherein the user's lower jaw is displaced by predetermined increments, the method for adaptively controlling a mandibular advancement device, the method comprising the steps of:
fitting a first member substantially over a portion of the teeth of the upper jaw of a user;
fitting a second member substantially over a portion of the teeth of the lower jaw of user; engaging an engagement arrangement to maintain the lower jaw of the user in a predetermined protruding position relative to the upper jaw of the user and the natural biting position of the lower jaw;
removing the first member substantially over a portion of the teeth of the upper jaw of a user;
fitting a second first member substantially over a portion of the teeth of the upper jaw of a user; and
engaging an engagement arrangement to maintain the lower jaw of the user in a predetermined protruding position relative to the upper jaw of the user and the natural biting position of the lower jaw.

It will be understood that the second predetermined protruding position by the engagement of the second first member and the second member can be more or less advanced than the first predetermined protruding position by the engagement the initial first member and second member.

The method further comprising the steps of: removing the second first member substantially over the portion of the teeth of the upper jaw of a user; fitting a third first member substantially over a portion of the teeth of the upper jaw of a user; and engaging an engagement arrangement to maintain the lower jaw of the user in a predetermined protruding position relative to the upper jaw of the user and the natural biting position of the lower jaw.

It will be understood that the third predetermined protruding position by the engagement the third first member and the second member can be more or less advanced than the first predetermined protruding position by the engagement the initial first member and second member and/or the second predetermined protruding position by the engagement the second first member and second member.

A method for adaptively controlling a mandibular advancement device wherein the user's lower jaw is displaced by a predetermined increment of 0.01 mm.

A method for adaptively controlling a mandibular advancement device wherein the user's lower jaw is displaced by a predetermined increment of at least 0.01 mm.

A method for adaptively controlling a mandibular advancement device wherein the user's lower jaw is displaced by a predetermined increment of at least 0.02 mm.

A method for adaptively controlling a mandibular advancement device wherein the user's lower jaw is displaced by a predetermined increment of at least 0.05 mm.

A method for adaptively controlling a mandibular advancement device wherein the user's lower jaw is displaced by a predetermined increment of at least 0.05 mm.

A method for adaptively controlling a mandibular advancement device wherein the user's lower jaw is displaced by a predetermined increment of at least 0.1 mm.

A method for adaptively controlling a mandibular advancement device wherein the user's lower jaw is displaced by a predetermined increment of at least 0.15 mm.

A method for adaptively controlling a mandibular advancement device wherein the user's lower jaw is displaced by a predetermined increment of at least 0.2 mm.

A method for adaptively controlling a mandibular advancement device wherein the user's lower jaw is displaced by a predetermined increment of less than and/or equal to 50 mm.

A method for adaptively controlling a mandibular advancement device wherein the user's lower jaw is displaced by a predetermined increment of greater than 50 mm.

A method for adaptively controlling a mandibular advancement device wherein the user's lower jaw is displaced by a predetermined increment of less than and/or equal to 40 mm.

A method for adaptively controlling a mandibular advancement device wherein the user's lower jaw is displaced by a predetermined increment of less than and/or equal to 30 mm.

A method for adaptively controlling a mandibular advancement device wherein the user's lower jaw is displaced by a predetermined increment of less than and/or equal to 20 mm.

A method for adaptively controlling a mandibular advancement device wherein the user's lower jaw is displaced by a predetermined increment of less than and/or equal to 10 mm.

A method for adaptively controlling a mandibular advancement device wherein the user's lower jaw is displaced by predetermined increments in the range of 0.2 mm to 10 mm.

A method for adaptively controlling a mandibular advancement device wherein the user's lower jaw is displaced by predetermined increments in the range of 0.25 mm to 7.5 mm.

A method for adaptively controlling a mandibular advancement device wherein the user's lower jaw is displaced by predetermined increments in the range of 0.3 mm to 6.5 mm.

A method for adaptively controlling a mandibular advancement device wherein the user's lower jaw is displaced by predetermined increments in the range of 0.4 mm to 0.6 mm.

Accordingly, the present invention provides a mandibular advancement device comprising:

a first member, the first member configured to fit substantially over a portion of the teeth of the upper jaw of a user, and a second member, the second member configured to fit substantially over a portion of the teeth of the lower jaw of the user, and an engagement arrangement, configured to be engagable upon a forward manipulation of the lower jaw by the user, to maintain the lower jaw of the user in a predetermined protruding position relative to the upper jaw of the user and the natural biting position of the lower jaw, wherein the engagement arrangement comprises articulation restriction means to restrict articulation of the lower jaw of the user when the engagement arrangement is engaged and the lower jaw of the user is in the predetermined protruding position.

Ideally, the articulation restriction means is located in an occlusal area where the teeth of the upper jaw would normally contact the teeth of the lower jaw.

Preferably, the articulation restriction means comprises a first member restrictive element on the first member.

Ideally, the articulation restriction means comprises a second member restrictive element on the second member.

Preferably the first member restrictive element and/or the second member restrictive element of the articulation restriction means are configured to protrude a short distance from a main body of the first member and/or the second member to interface, interact and/or otherwise engage with one another when the engagement arrangement is engaged to restrict articulation of the lower jaw of the user when in the predetermined protruding position.

Ideally, the first member restrictive element and/or the second member restrictive element of the articulation restriction means are configured to protrude a short distance from a main body of the engagement arrangement to interface, interact and/or otherwise engage with one another when the engagement arrangement is engaged to restrict articulation of the lower jaw of the user when in the predetermined protruding position.

It will be understood that articulation of the lower jaw relates to the natural movement of the lower jaw during opening. By natural movement of the lower jaw during opening it will be understood to be movement via the temporomandibular joint.

Advantageously, having a mandibular advancement device with an engagement arrangement provides the wearer with a simple and comfortable manual positional adjustment of the jaw positions beyond that of the prior art devices; one that can be achieved from the user's sleeping position with little disruption to the user. The simple forward manipulation is a natural movement of the lower jaw contrasted to the cumbersome adjustment mechanisms of the prior art which require that the mandibular advancement device be removed from the wearer's mouth, adjusted and subsequently reinserted or requires a mechanical adjustment carried out with an external adjustment device which must enter the wearer's mouth.

Further advantageously, having the engagement arrangement comprising articulation restriction means provides the wearer with a simple and more effective mandibular advancement device than that of the prior art devices; one that restricts the users jaw naturally and involuntarily articulating open and disengaging the engagement arrangement.

Preferably, the engagement arrangement comprises first member engagement means and second member engagement means.

Ideally, the first member engagement means and second member engagement means being configured to be operatively engagable with one another upon forward manipulation of the lower jaw by the user, to maintain the lower jaw of the user in a predetermined protruding position relative to the upper jaw of the user and the natural biting position of the lower jaw.

Preferably, the second member is moveable relative to the first member under the influence of the user moving their lower jaw forward and backwards to engage the protruding position.

Preferably, the second member is slidably moveable relative to the first member under the influence of the user moving their lower jaw forward and backwards to engage the protruding position.

Preferably, the first member engagement means protrudes a short distance from the first member in a direction towards the second member and the second member engagement means protrudes a short distance from the second member in a direction towards the first member when the first member and second member are positioned upon the teeth of the upper and lower jaw respectively Preferably, the engagement arrangement is located in an occlusal area where the teeth of the upper jaw would normally contact the teeth of the lower jaw.

Advantageously, having the engagement arrangement located within an occlusal area provides a comfortable location which will not irritate a user during use unlike conventional mandibular advancement devices which comprise bands or hooks etc. which run along the outside of teeth and could irritate the adjacent soft tissue of the user's cheek. Additionally, the engagement arrangement is located in the free space which is created when the lower jaw is moved forwards and downwards.

Further advantageously, the engagement arrangement located within an occlusal area enables the jaw to remain slightly and comfortably open. This reduces the likelihood of an airway obstruction.

Preferably, the engagement arrangement is located proximal to the anterior portion of the user's mouth when the first member and second member are fitted over a portion of the teeth of the upper jaw and lower jaw of the user.

Ideally, the engagement arrangement is located proximal to an anterior portion of the first member and/or second member when in use.

It will be appreciated that the anterior portion of the first and/or second member is the leading portion of the first member and second member during movement from the lower jaw resting position to the predetermined protruding position.

Preferably, the engagement arrangement is located proximal to the canine teeth of a user when the first member and second member are fitted over a portion of the teeth of the upper jaw and lower jaw of the user.

Ideally, the engagement arrangement is configured to permit lateral movement of the second member when the engagement arrangement is engaged Preferably, the second member engagement means is configured to permit lateral movement of the second member when the first member engagement means and the second member engagement means are engaged.

Advantageously, this configuration of the second member engagement means to enable lateral movements enables a comfortable and non-irritating fit which can accommodate natural lateral movements of the jaw which can occur naturally during sleep.

Preferably, the second member engagement means is configured to permit lateral movement of the second member when the first member engagement means and the second member engagement means are engaged between boundary elements.

Advantageously, the boundary elements restrict lateral movement so as to maintain the engagement between the first member engagement means and the second member engagement means.

Further advantageously, as individuals typically sleep on their side and/or move while asleep the boundary elements provide a more efficient mandibular advancement device and engagement mechanism than those found within conventional devices by preventing or greatly reducing the risk of accidental disengagement of the device during sleep, to the individuals sleeping positions and movements.

Ideally, the boundary elements are located upon the first member and/or second member.

Preferably, the boundary elements extend from a portion of the second member and/or the first member in a direction towards respective first member or second member.

Ideally, the boundary elements extend from a position proximal to the anterior portion of the first member and/or second member to a position located proximal to a posterior portion of the first member and/or second member when the first member and second member are fitted over a portion of the teeth of the upper jaw and lower jaw of the user.

Preferably, the boundary elements are positioned and configured to abut and/or contact at least partially with a portion of the first member engagement means or second member engagement means.

Ideally, the boundary elements are positioned and configured to abut and/or contact at least partially with an outer surface of the first member engagement means or second member engagement means.

Ideally, the boundary elements extend from a portion of the first member and/or second member proximal to the buccal portion of the teeth when the first member and/or second member are fitted over a portion of the teeth of the upper and lower jaw of the user.

Preferably, the first member and second member are separate members.

Preferably, the first member and second member are arcuate structures.

Advantageously, having the first member and second member being arcuate structures enables a comfortable and non-irritating fit of the mandibular advancement device as the structure mimics the shape of the user's jaw.

Preferably, the engagement arrangement comprises a pair of first member engagement means and a pair of second member engagement means, most preferably on opposing locations of the arcuate first member and arcuate second member respectively.

Preferably, the engagement arrangement comprises a pair of first member engagement means radially equispaced from the centre of curvature of the arc of the first member and a pair of second member engagement means radially equispaced from the centre of curvature of the arc of the second member.

Advantageously, having a pair of first member engagement means and a pair of second member engagement means on opposing locations of the arc enables the user's lower jaw to remain comfortably in a natural balance and equilibrium. The arrangement further maintains the lower jaw in alignment and in a stable position with a more secure engagement between the lower and upper jaw.

Preferably, the articulation restriction means comprises a pair of first member restrictive elements.

Ideally, the articulation restriction means comprises a pair of second member restrictive elements.

Preferably, the pair of first member restrictive elements and second member restrictive elements are located at opposing locations of the first member and second member respectively.

Ideally, the pair of first member restrictive elements are radially equispaced from the centre of curvature of the arc of the first member.

Preferably, the pair of second member restrictive elements are radially equispaced from the centre of curvature of the arc of the second member.

Advantageously, having a pair of first member restrictive elements and a pair of second member restrictive elements on opposing locations of the arc enables the user's lower jaw to remain comfortably in a natural balance and equilibrium.

Further advantageously, the arrangement further maintains the lower jaw in alignment and in a stable position with a more secure engagement between the user's lower jaw and upper jaw.

Preferably, first member engagement means and second member engagement means are partially embedded within their respective first and/or second member Preferably, the engagement arrangement is configured to releasably engage in use.

Preferably, the engagement arrangement is configured to disengage under the influence of the user moving their lower jaw forward beyond the protruding position.

Preferably, the engagement arrangement is configured to enable the return the second member to the user's natural biting position of the lower jaw by natural articulative movement of the lower jaw.

Preferably, once the engagement arrangement is disengaged the user can return the lower jaw to the natural biting position by simply opening their mouth.

Preferably, the engagement arrangement is configured to enable the articulation restriction means to releasably engage in use.

Preferably, the engagement arrangement is adapted to enable the first member engagement means and second member engagement means to releasably engage in use.

Preferably, the engagement arrangement is configured to enable the first member restrictive element of the articulation restriction means and the second member restrictive element to releasably engage in use.

Preferably, the first member restrictive element and/or the second member restrictive element of the articulation restriction means are configured to interface, interact and/or otherwise engage with one another.

Ideally, the first member restrictive element and/or second member restrictive element of the articulation restriction means are configured to interlock with one another.

Preferably, the first member restrictive element and/or second member restrictive element of the articulation restriction means are configured to interlock with one another by means of an interlocking joint.

Ideally, the first member restrictive element and/or second member restrictive element of the articulation restriction means comprise an indentation.

Preferably, the indentation of the first member restrictive element and/or second member restrictive element of the articulation restriction means co-operates with a protruding element of the respective second member restrictive element and/or first member restrictive element of the articulation restriction means.

Ideally, the indentation of the first member restrictive element and/or second member restrictive element of the articulation restriction means is configured to correspond to the shape of the co-operating protruding element of the respective second member restrictive element and/or first member restrictive element of the articulation restriction means.

Advantageously, an indentation on either or both of the first member restrictive element and second member restrictive element which co-operates with a protruding element of the respective second member restrictive element and first member restrictive element increases the contact area between the first member restrictive element and second member restrictive element when engaged with one another. This improves the efficiency of the device and reduces the stresses and load placed upon the engaging portions of the device resulting in a device which is less likely to fracture and/or break.

Ideally, the indentation of the first member restrictive element is truncated in a direction opposing an anterior portion of the first member.

Preferably, the indentation of the second member restrictive element is truncated in a direction towards an anterior portion of the second member.

Ideally, the indentation is a V-shaped indentation.

Alternatively, the indentation is a C or U-shaped indentation.

Further, alternatively, the indentation is a B, D, M, S or W-shaped indentation.

Preferably, the protruding element of the articulation means which co-operates with the indentation of the second member restrictive element and/or first member restrictive element corresponds in shape to that of the indention.

Advantageously, this corresponding in shape provides a more efficient engagement between the first member and second member.

Preferably, the first member restrictive element and the second member restrictive element of the articulation restriction means comprise abutment portions.

Ideally, the first member restrictive element of the articulation restriction means is couplable to at least one of the pair of first member engagement means.

Preferably, the first member restrictive element of the articulation restriction means is integral to at least one of the pair of first member engagement means.

Ideally, the first member restrictive element of the articulation restriction means and at least one of the pair of first member engagement means are a unitary unit.

Preferably, the second member restrictive element of the articulation restriction means is couplable to at least one of the pair of second member engagement means.

Ideally, the second member restrictive element of the articulation restriction means is integral to at least one of the pair of second member engagement means.

Preferably, the second member restrictive element of the articulation restriction means and at least one of the pair of second member engagement means are a unitary unit.

Ideally, the articulation restriction means and the engagement arrangement are a unitary unit.

Preferably, abutment portion of the first member restrictive element and the abutment portion of the second member restrictive element of the articulation restriction means are configured to interface, interact and/or otherwise engage with one another.

Preferably, abutment portion of the first member restrictive element and the abutment portion of the second member restrictive element of the articulation restriction means are configured to interlock with one another.

Preferably, the abutment portion of the first member restrictive element is located proximal to a leading edge of the first member engagement means.

Preferably, the abutment portion of the second member restrictive element is located proximal to a trailing edge of the second member engagement means.

Ideally, the abutment portion of the first member restrictive element and/or the second member restrictive element is configured to form the indentation of the first member restrictive element and/or second member restrictive element of the articulation restriction means.

Preferably, the abutment portion of the first member restrictive element and/or the second member restrictive element is configured to form the protruding element of the first member restrictive element and/or second member restrictive element of the articulation restriction means.

Preferably, the abutment portions of the first member restrictive element and/or the second member restrictive element are tapered to a point.

Ideally, the abutment portions of the first member restrictive element and/or the second member restrictive element taper to a central portion of the abutment portion.

Preferably, the abutment portion of the first member restrictive element and/or the second member restrictive element comprise one or more abutment surfaces which taper towards a central portion of the abutment portion.

Ideally, the tapering of the abutment portion and/or abutment surfaces form the V-shaped indentation and co-operating protruding element of the first member restrictive element and/or the second member restrictive element.

Preferably, the abutment portions are bevelled portions.

Ideally, the bevelled portions are located upon the first member engagement means and the second member engagement means.

Preferably, the bevelled portions of the first member engagement means and the second member engagement means are substantially parallel to one another when the jaw is in its natural biting position and in the protruding position.

Ideally, the first member engagement means and second member engagement means are adjacent one another when the first engagement means and the second engagement means are engaged with one another Preferably, the first member engagement means and second member engagement means are adjacent one another when the jaw is in its natural biting position and when the jaw is in its predetermined protruding position.

Preferably, the first member engagement means and second member engagement means are at least partially overlapping when the jaw is in its natural biting position and at least partially overlapping when the jaw is in its protruding position.

Preferably, when in the natural biting position, the longitudinal plane of the first member engagement means is substantially parallel to the longitudinal plane of the second member engagement means.

Preferably, when in the protruding position the longitudinal plane of the first member engagement means and the longitudinal plane of the second member engagement means are coincident.

Preferably, the first member engagement means and second member engagement means are mutually opposing when the jaw is in its natural biting position and when the jaw is in its protruding position.

Preferably, when in the natural biting position and upon movement of the second member from the natural biting position to the protruding position, the second member engagement means is spatially displaced from opposing the first member engagement means along a horizontal plane to opposing the first member engagement means along a substantially vertical plane under the influence of a user moving their lower jaw forward.

Preferably, the engagement arrangement further comprises braking means to halt the forward sliding movement of the lower jaw of the user.

Advantageously, the braking means signals to the wearer that no further forward movement of the lower jaw is necessary to engage the engagement arrangement. Once the braking means is reached from the wearers forward movement of the lower jaw, to engage with the engagement arrangement the wearer simply slides their lower jaw back in the direction of the natural biting position.

Further advantageously, when at sleep an individual's lower jaw can undergo movement whether forward or side to side which can lead to an ineffective engagement or disengagement of the first and second member. Having braking means reduces this risk of disengagement and provides a more effective engagement of the first and second member.

Preferably, the braking means is a protrusion protruding from a portion of the second member.

Ideally, the braking means is a protrusion protruding from a portion of the second member in a direction towards a portion of the first member when in use.

Preferably, the braking means is a ridge, rib or dimple within the second member engagement means.

Alternatively, the braking means is a polygonal shaped protrusion.

Preferably, the braking means of the second member is proximal to an opposing portion of the second member from that of the articulation restriction means.

Ideally, the braking means is configured to interface, interact and/or otherwise engage with a contact portion of the first member engaging means.

Preferably, the braking means is configured to interlock with a contact portion of the first member engaging means.

Preferably, the braking means is configured to interface, interact and/or otherwise engage with a contact portion of the first member engaging means located at a position opposing to that of the first member restrictive element.

Ideally, the braking means comprises braking abutment portions to abut and/or contact a contact portion of the first member engaging means.

Ideally, a portion of the braking means is angled forward in a direction towards the engagement means of the mandibular advancement device.

Preferably, the contact portion of the first member engaging means is an angled portion.

Preferably, the angled portion of the braking means interacts, abuts and/or otherwise engages with the angled contact portion of the first member engaging means.

Ideally, the angled portions of the contact portion of the first member engaging means and the angled portion of braking means are substantially parallel to one another when in the natural biting position, in the protruding position and in the braking position.

Advantageously, the braking means acts to prevent the device disengaging in the event that the user inadvertently pushes their jaw forward during sleep. The angled portion of the braking means on the second member and the contact portion of the first member engaging means are angled and inclined at the same or similar angle so that if the user pushes their jaw inadvertently forward an engagement occurs between the braking means and the first member engagement means which makes it difficult for the user to articulate their jaw and as a result the user will relax their lower jaw back into the predetermined protruding position wherein the first member engagement means and second member engagement means are engaged with one another.

Preferably, the engagement arrangement comprises guide means to guide the first member engagement means to the second member engagement means for the securement of the second member in the protruding position.

Preferably, the guide means extends between articulation restriction means and the braking means.

Preferably, in use and prior to instances of sleep the user inserts the mandibular advancement device into their mouth such that the first member of fitted substantially over a portion of the teeth of the upper jaw and that the second member is fitted substantially over a portion of the teeth of the lower jaw, the user naturally bites down on the second member placing the jaw into its natural biting position, the user manipulates the lower jaw forward into a protruding position, in response to this forward movement of the lower jaw by the user the second member slidably moves and the first member engagement means engages a guide means located on the second member, forward movement of the lower jaw continues until the user reaches the braking means, then the user initiates the return of the lower jaw to the natural biting position wherein the first member engagement means is guided by the guide means to the second member engagement means for the securement of the second member in the protruding position.

Accordingly, the present invention provides a sports mouthguard for optimising the breathing input and/or output of a user by improved airflow, preferably, while providing protection from physical impact comprising:
- a first member, the first member configured to fit substantially over a portion of the teeth of the upper jaw of a user, and
- a second member, the second member configured to fit substantially over a portion of the teeth of the lower jaw of the user, and
- an engagement arrangement, the engagement arrangement comprising first member engagement means protruding a short distance from the first member in a direction towards the second member second member engagement means protruding a short distance from the second member in a direction towards the first member when the first member and second member are positioned upon the teeth of the upper and lower jaw respectively, the first member engagement means and second member engagement means being configured to be operatively engagable with one another upon forward manipulation of the lower jaw by the user, to maintain the lower jaw of the user in a predetermined protruding position relative to the upper jaw of the user and the natural biting position of the lower jaw,
- wherein the engagement arrangement further comprises articulation restriction means, the articulation restriction means configured to restrict articulation of the lower jaw of the user when in the predetermined protruding position Advantageously, as a result of the advanced positioning of the mandible unlike conventional mouthguards, the muscles are stretched and strengthened minimising the narrowing of the pharynx due to muscular relaxation. This stretching and strengthening of the muscles reduces turbulence within the airway. By keeping the jaw slightly ajar airflow is also improved through the lips and mouth beyond that of the conventional mouthguard. This increased and improved airflow can increase athletic performance by optimising breathing beyond that of the conventional mouthguard utilised by athletes participating in sport.

The skilled man will appreciate that all preferred or optional features of the invention described with reference to only some aspects or embodiments of the invention may be applied to all aspects of the invention.

It will be appreciated that optional features applicable to one aspect of the invention can be used in any combination, and in any number. Moreover, they can also be used with any of the other aspects of the invention in any combination and in any number. This includes, but is not limited to, the dependent claims from any claim being used as dependent claims for any other claim in the claims of this application.

The invention will now be described with reference to the accompanying drawing which shows by way of example embodiments of an apparatus in accordance with the invention.

Figure 1:
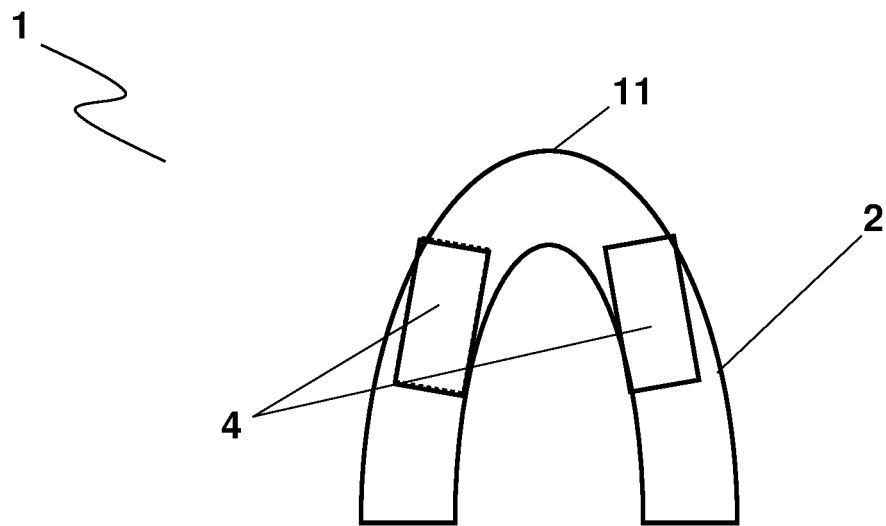
FIG. 1 is a schematic diagram showing the first member and second member of the mandibular advance kit/device in the jaw's natural biting position.
Figure 3:
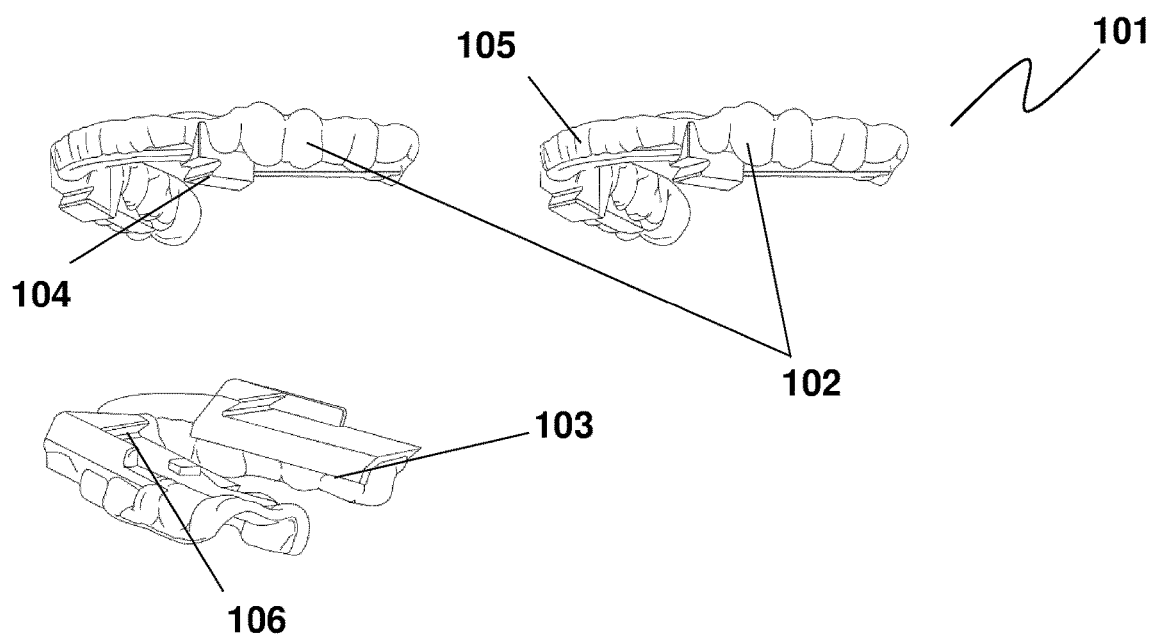
FIG. 3 is a perspective view of the first embodiment of the mandibular advancement kit with a plurality of first members and at least one second member.
Figure 4:
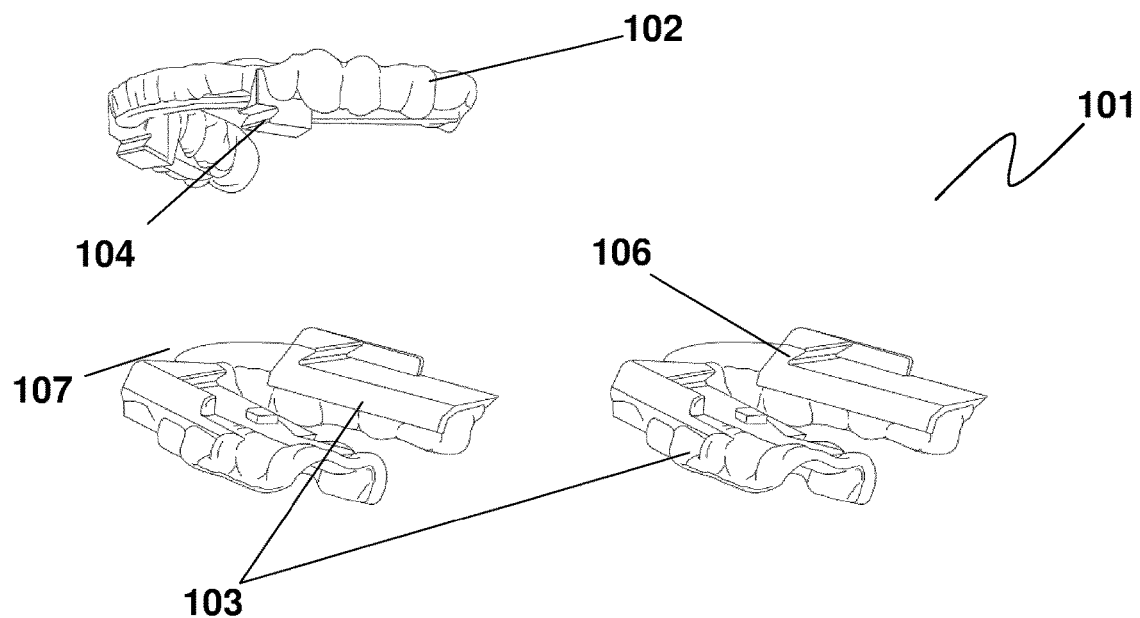
FIG. 4 is a perspective view of the second embodiment of the mandibular advancement kit with a plurality of second members and at least one first member.

In the drawings there is shown a mandibular advancement kit 101. The mandibular advancement kit 101 having a plurality of first members 102 and at least one second member 103 or at least one first member 102 and a plurality of second members 103, and an engagement arrangement 104, configured to be engageable between a first member 102 and a second member 103, to maintain the lower jaw of the user in a predetermined protruding position (see FIG. 2) relative to the upper jaw of the user and the natural biting position of the lower jaw (FIG. 1). The first member(s) configured to fit substantially over a portion of the teeth of the upper jaw of a user and the second member(s) configured to fit substantially over a portion of the teeth of the lower jaw of the user. Each first member 102 is mutually interchangeable with another first member 102 for being engageable to the second member 103; FIG. 3. In an alternative (FIG. 4), each second member 103 is mutually interchangeable with another second member 103 for being engageable to the first member 102. Each first member 102 and/or second member 103 of the respective plurality are interchangeable with another from said plurality to advance the user's lower jaw at predetermined increments. The kit 101 has at least one first member 102 and/or at least one second member 103 wherein the user's lower jaw is displaced by predetermined increments as the members (102, 103) are interchanged.

Having a mandibular advancement kit 101 having interchangeable first members 102 and/or second members 103 enables the user to enjoy varying degrees of advancement with a comfortable adjustment method beyond that of conventional mandibular advancement devices which require physical means of adjustment and readjustment typically by means of screws and straps. Further, conventional mandibular advancement devices which require physical means of adjustment and readjustment are prone to fracturing at the point of attachment between the device and means of adjustment/readjustment, having interchangeable components (102, 103) negates and obliviates this risk of fracture.

The user's lower jaw is displaced by predetermined increments in the range of 0.0.01 mm to 50 mm; depending on user requirements.

The kit 101 comprising multiple first members 102 wherein each first member 102 has first member engagement elements 104 located at different positions proximal to the anterior portion 105 of the respective first member 102. The first member engagement elements are engagable with a second member engagement element 106 on the second member 103. Alternatively, the kit 101 has multiple first members 102 wherein each first member 102 comprises first member engagement elements extending longitudinally to varying lengths.

The kit 101 comprising multiple second members 103 wherein each second member 103 comprises second member engagement elements 106 located at different positions proximal to the anterior portion 107 of the respective second member 103. The second member engagement elements 106 are engagable with a first member engagement element 104 on the first member 102. Alternatively, the kit 101 comprising multiple second members 103 wherein each second member 103 has second member engagement elements 106 extending longitudinally to varying lengths.

Having varying positions and/or varying lengths of first member engagement elements 104 and/or second member engagement elements 106 provides the user with a mandibular advancement device with a comfortable and stepped adjustment/readjustment method which is bespoke to the individual user without cumbersome and time-consuming adjustments of conventional mandibular advancement devices.

In the drawings there is further shown a mandibular advance advancement device generally indicated by the numeral 1. The mandibular advancement device 1 having a first member 2 and a second member 3. The first member 2 is configured to fit substantially over a portion of the teeth of the upper jaw of a user (not shown) and the second member 3 is configured to fit substantially over a portion of the teeth of the lower jaw of the user (not shown). The mandibular advancement device 1 further has an engagement arrangement 4, configured to be engagable upon a forward manipulation of the lower jaw (not shown) by the user, to maintain the lower jaw (not shown) of the user in a predetermined protruding position relative to the upper jaw (not shown) of the user and the natural biting position of the lower jaw (not shown); see FIG. 2. The engagement arrangement further has articulation restriction arrangement 5. The articulation restriction arrangement 5 restrict articulation of the lower jaw of the user (not shown) when the engagement arrangement 4 is engaged and the lower jaw of the user (not shown) is in the predetermined protruding position; illustrated in FIG. 2.

The articulation restriction arrangement 5 comprises a first member restrictive element 6 on the first member 2 and a second member restrictive element 7 on the second member 3. The first member restrictive element 6 and/or the second member restrictive element 7 of the articulation restriction arrangement 5 are configured to protrude a short distance from a main body of the respective first member 2 and/or second member 3 to interface, interact and/or otherwise engage with one another when the engagement arrangement is engaged to restrict articulation of the lower jaw of the user (not shown) when in the predetermined protruding position. It will be understood that articulation of the lower jaw (not shown) relates to the natural movement of the lower jaw (not shown) during opening. By natural movement of the lower jaw (nots shown) during opening it will be understood to be movement via the temporomandibular joint of the user (not shown).

Advantageously, having a mandibular advancement device 1 with an engagement arrangement 4 provides the wearer with a simple and comfortable manual positional adjustment of the jaw positions beyond that of the prior art devices; one that can be achieved from the user's sleeping position with little disruption to the user. The simple forward manipulation is a natural movement of the lower jaw (not shown) contrasted to the cumbersome adjustment mechanisms of the prior art which require that the mandibular advancement device 1 be removed from the wearer's mouth, adjusted and subsequently reinserted or requires a mechanical adjustment carried out with an external adjustment device which must enter the wearer's mouth.

Further advantageously, having the engagement arrangement 4 comprising an articulation restriction arrangement 5 the wearer with a simple and more effective mandibular advancement device 1 than that of the prior art devices; one the restricts the users jaw (not shown) naturally and involuntarily articulating open and disengaging the engagement arrangement.

The engagement arrangement 4 comprises first member engagement component 8 and second member engagement component 9. The first member engagement component 8 and second member engagement component 9 being configured to be operatively engagable with one another upon forward manipulation of the lower jaw (not shown) by the user, to maintain the lower jaw (not shown) of the user in a predetermined protruding position relative to the upper jaw of the user and the natural biting position of the lower jaw; see FIG. 2. The second member 3 is moveable relative to the first member 2 under the influence of the user moving their lower jaw (not shown) forward and backwards to engage the protruding position; see FIG. 2. The first member engagement component 8 protrudes a short distance from the first member 2 in a direction towards the second member 3 and the second member engagement component 9 protrudes a short distance from the second member 3 in a direction towards the first member 1 when the first member 2 and second member 3 are positioned upon the teeth of the upper and lower jaw (not shown) respectively.

The engagement arrangement 4 is located in an occlusal area 10 where the teeth of the upper jaw would normally contact the teeth of the lower jaw. Advantageously, having the engagement arrangement 4 located within an occlusal area provides a comfortable location which will not irritate a user during use unlike conventional mandibular advancement devices which comprise bands or hooks etc. which run along the outside of teeth and could irritate the adjacent soft tissue of the user's cheek. Additionally, the engagement arrangement is located in the free space which is created when the lower jaw is moved forwards and downwards. Further advantageously, the engagement arrangement 4 located within an occlusal area enables the jaw to remain slightly and comfortably open. This reduces the likelihood of an airway obstruction.

The engagement arrangement 4 is located proximal to the anterior portion 11 of the user's mouth when the first member 2 and second member 3 are fitted over a portion of the teeth of the upper jaw and lower jaw of the user (not shown). The engagement arrangement 4 is located proximal to the canine teeth of a user (not shown) when the first member 2 and second member 3 are fitted over a portion of the teeth of the upper jaw and lower jaw of the user (not shown). The engagement arrangement 4 is located proximal an anterior portion 12 of the first member 2 and second member 3 when in use and fitted upon the teeth of the wearer. It will be appreciated that the anterior portion 12 of the first member 2 and second member 3 is a leading portion of the first member 2 and second member 3 during movement from the jaw resting position to the predetermined protruding position.

The engagement arrangement 4 is configured to permit lateral movement of the second member 3 when the engagement arrangement 4 is engaged. It is the second member engagement component 9 which is configured to permit lateral movement of the second member 3 when the first member engagement component 8 and second member engagement component 9 are engaged. Advantageously, this configuration of the second member engagement component 9 to enable lateral movements enables a comfortable and non-irritating fit which can accommodate natural lateral movements of the jaw which can occur naturally during sleep. The second member engagement component 9 is configured to permit lateral movement of the second member 3 when the first member engagement component 8 and the second member engagement component are engaged between boundary elements 13. These boundary elements 13 restrict lateral movement so as to maintain the engagement between the first member engagement component 8 and the second member engagement component 9. Further advantageously, as individuals typically sleep on their side and/or move while asleep the boundary elements 13 provide a more efficient mandibular advancement device 1 and engagement mechanism than those found within conventional devices by preventing or greatly reducing the risk of accidental disengagement of the device during sleep, to the individuals sleeping positions and movements.

The boundary elements 13 are located upon the first member 2 and/or second member 3 (most preferably upon the second member 3) and proximal to the buccal portion of the teeth when the first member 2 and/or second member 3 are fitted over a portion of the teeth of the upper and lower jaw of the user. They boundary elements 13 and extend from a position proximal to the anterior portion of the first member and/or second member 12 to a position located proximal to a posterior portion of the first member and/or second member 201 when the first member 2 and second member 3 are fitted over a portion of the teeth of the upper jaw and lower jaw of the user.

The boundary elements 13 are positioned and configured to abut and/or contact at least partially with a portion 202 of the first member engagement component 8 or second member engagement component 9.

The first member 2 and second member 3 are separate members of arcuate structures. Advantageously, having the first member 2 and second member 3 being arcuate structures enables a comfortable and non-irritating fit of the mandibular advancement device 1 as the structure mimics the shape of the user's jaw. The first member engagement component 8 and second member engagement component 9 are partially embedded within their respective first 2 and/or second 3 member.

The engagement arrangement 4 comprises a pair of first member engagement components 8 and a pair of second member engagement components 9, most preferably on opposing locations of the arcuate first member 2 and arcuate second member 3 respectively. The pair of first member engagement components 8 radially equispaced from the centre of curvature of the arc of the first member 2 and the pair of second member engagement components 9 radially equispaced from the centre of curvature of the arc of the second member 3. Advantageously, having a pair of first member engagement components 8 and a pair of second member engagement components 9 on opposing locations of the arc enables the user's lower jaw (not shown) to remain comfortably in a natural balance and equilibrium. The arrangement further maintains the lower jaw in alignment and in a stable position with a more secure engagement between the user's lower and upper jaw.

The articulation restriction arrangement 5 comprises a pair of first member restrictive elements 6 and a pair of second member restrictive elements 7, most preferably on opposing locations of the arcuate first member 2 and arcuate second member 3 respectively. The pair of first member restrictive elements 6 radially equispaced from the centre of curvature of the arc of the first member 2 and the pair of second member restrictive elements 7 radially equispaced from the centre of curvature of the arc of the second member 3. Advantageously, having a pair of first member restrictive elements 6 and a pair of second member restrictive elements 7 on opposing locations of the arc enables the user's lower jaw (not shown) to remain comfortably in a natural balance and equilibrium. The arrangement further maintains the lower jaw in alignment and in a stable position with a more secure engagement between the user's lower and upper jaw.

The engagement arrangement 4 is configured to releasably engage in use. The engagement arrangement 4 is configured to disengage under the influence of the user moving their lower jaw (not shown) forward beyond the protruding position and the engagement arrangement 4 is configured to enable the return the second member 3 to the user's natural biting position of the lower jaw by natural articulative movement of the lower jaw i.e. once the engagement arrangement 4 is disengaged the user can return the lower jaw to the natural biting position by simply opening their mouth.

The engagement arrangement 4 is configured to enable the articulation restriction arrangement 5 to releasably engage in use. The engagement arrangement 4 is adapted to enable the first member engagement components 8 and second member engagement components 9 to releasably engage in use. The engagement arrangement 4 is configured to enable the first member restrictive element 6 of the articulation restriction arrangement 5 and the second member restrictive element 7 to releasably engage in use.

The first member restrictive element 6 of the articulation restriction arrangement 5 is couplable to at least one of the pair of first member engagement components 8. The first member restrictive element 6 of the articulation restriction arrangement 5 is integral to at least one of the pair of first member engagement components 8. The first member restrictive element 6 of the articulation restriction arrangement 5 and at least one of the pair of first member engagement components 8 are a unitary unit. Likewise, the second member restrictive element 7 of the articulation restriction arrangement 5 is couplable to at least one of pair of second member engagement components 9. The second member restrictive element 7 of the articulation restriction arrangement 5 is integral to at least one of pair of second member engagement components 9. The second member restrictive element 7 of the articulation restriction arrangement 5 and at least one of the pair of second member engagement components 9 are a unitary unit. Ideally, both first member engagement components 8 and first members restrictive elements 6 are unitary units and both second member engagement components 9 and second members restrictive elements 7 are unitary units respectively.

Figure 5:
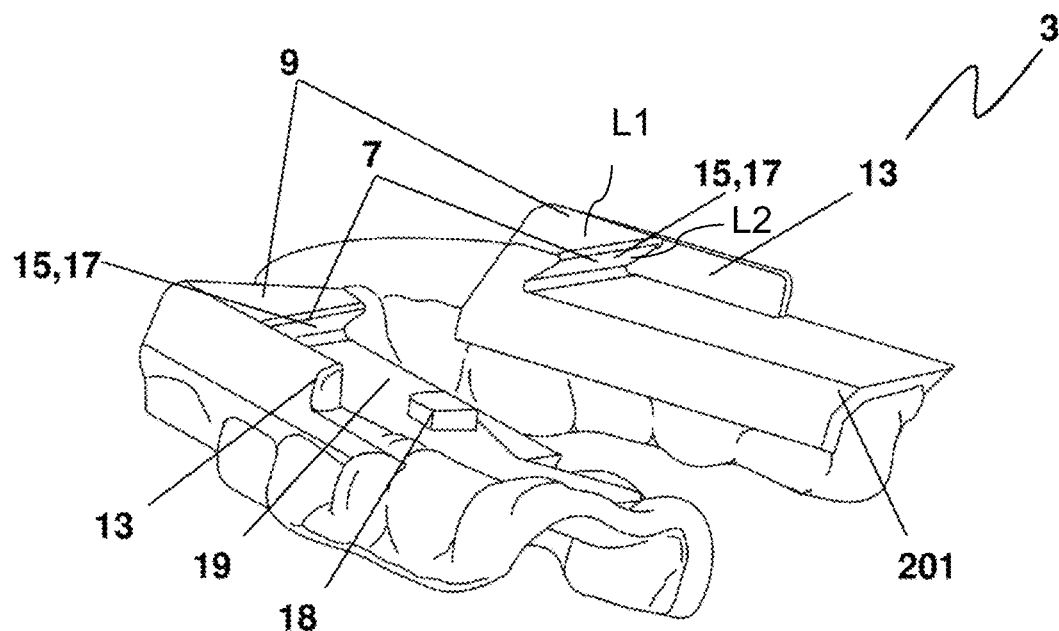
FIG. 5 is a perspective view of the second member of the mandibular advancement device.
Figure 6:
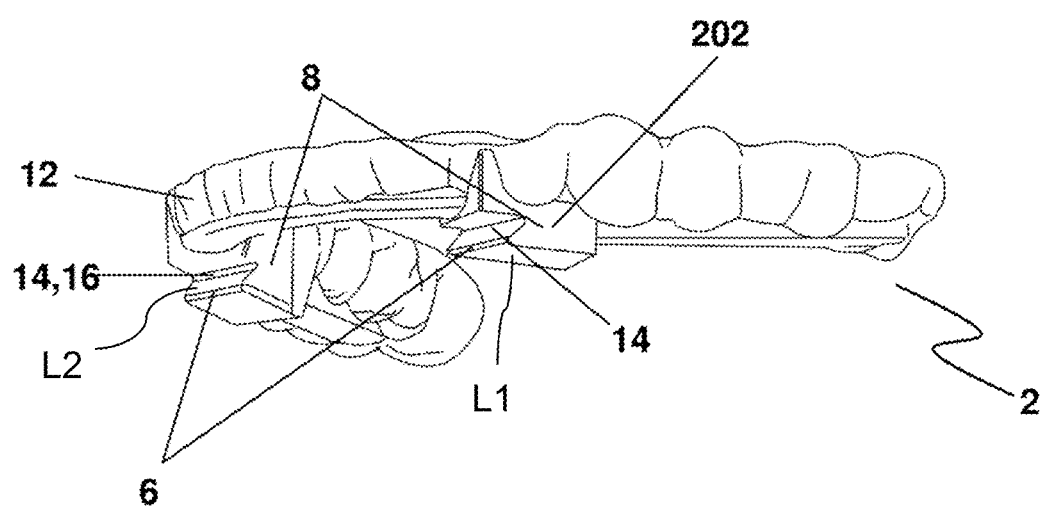
FIG. 6 is a perspective view of the first member of the mandibular advancement device.
Figure 7:
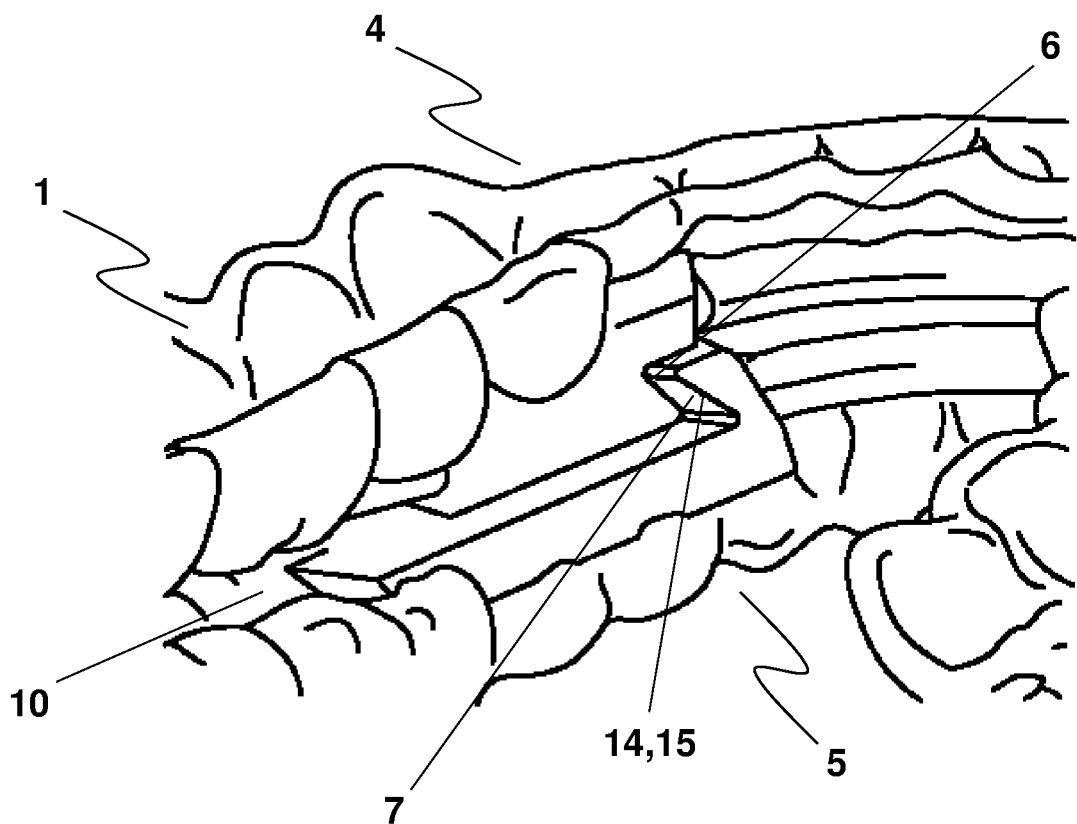
FIG. 7 is a partial perspective view of the first member and second member of the mandibular advancement device in engagement with one another.
Figure 8:
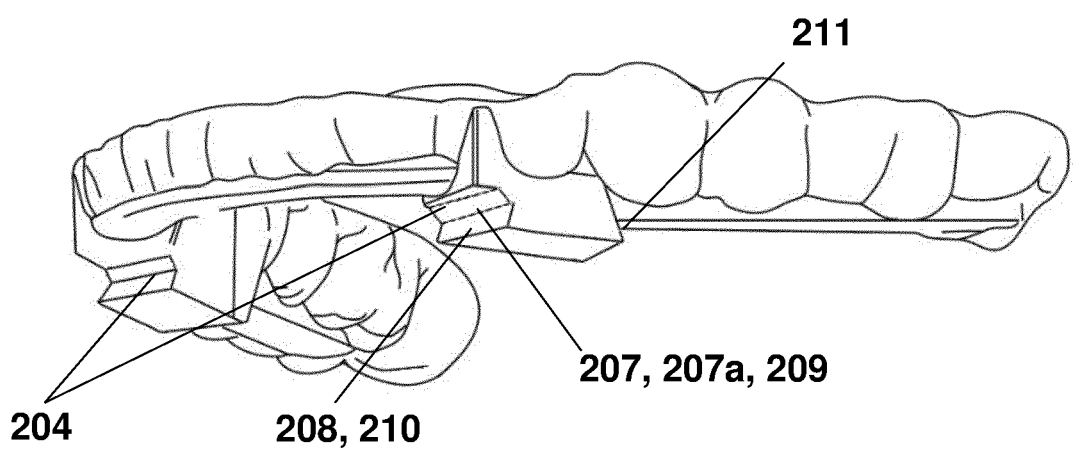
FIG. 8 is a perspective view of a first member of the mandibular advancement device having an alternate embodiment of the engagement arrangement.
Figure 9:
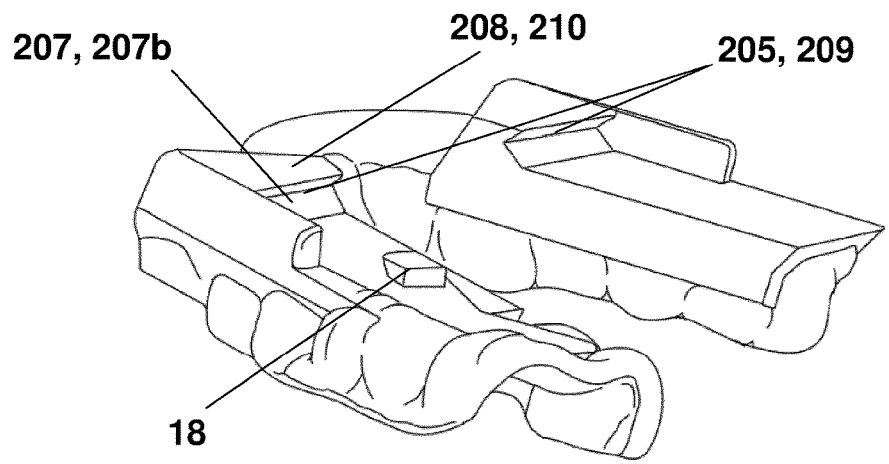
FIG. 9 is a perspective view of a second member of the mandibular advancement device having an alternate embodiment of the engagement arrangement.
Figure 10:
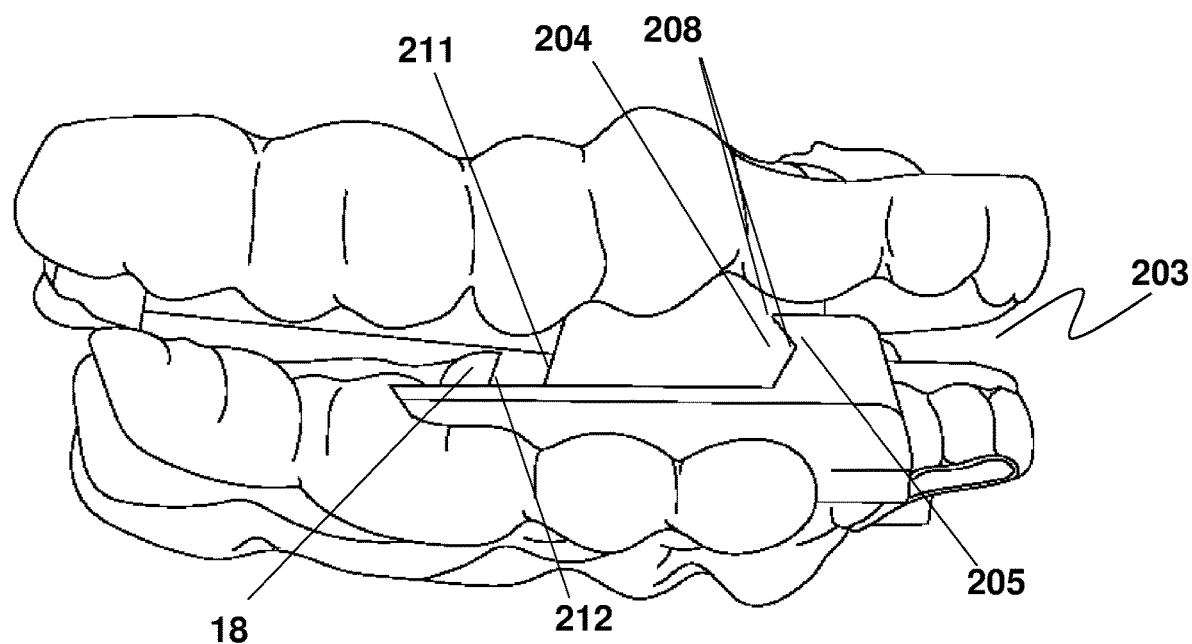
FIG. 10 is a side view of the first member and second member of the mandibular advancement device in engagement with one another having an alternate embodiment of the engagement arrangement.
Figure 11:
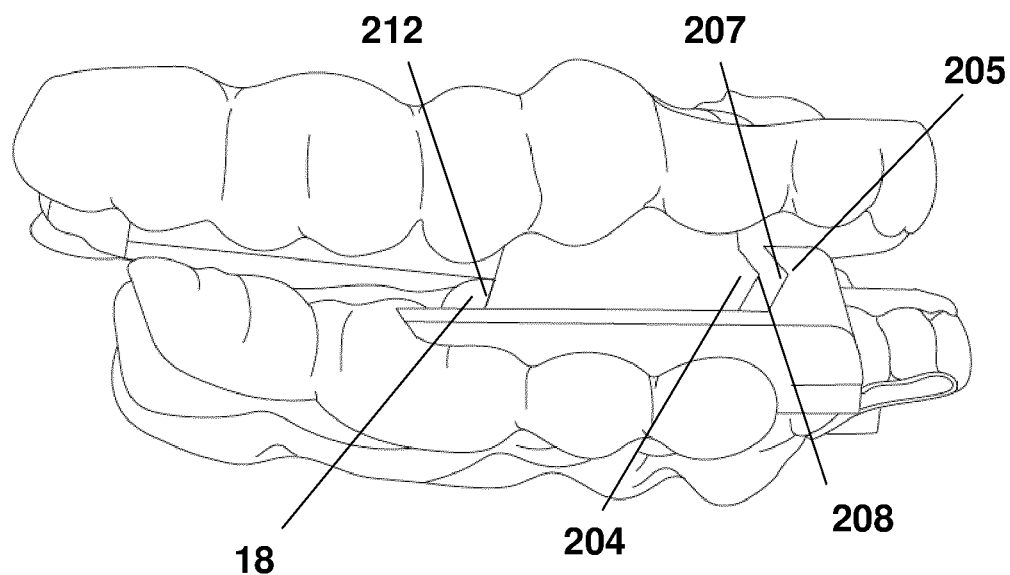
FIG. 11 is a side view of the first member and the braking component of the mandibular advancement device in engagement with one another having an alternate embodiment of the engagement arrangement.

The first member restrictive element 6 and the second member restrictive element 7 of the articulation restriction arrangement 5 comprise abutment portions (14 and 15). The abutment portions (14 and 15) of the first member restrictive element 6 and the second member restrictive element 7 of the articulation restriction arrangement 5 are configured to interface, interact and/or otherwise engage with one another. As shown in FIG. 5 the abutment portions 14, 15 of the first member restrictive element 6 and the second member restrictive element 7 of the articulation restriction arrangement 5 are configured to interlock with one another.

The abutment portion 14 of the first member restrictive element 6 is located proximal to a leading edge 16 of the first member engagement component 8. The abutment portion 15 of the second member restrictive element 7 is located proximal to a trailing edge 17 of the second member engagement component 9. As seen in the figures, the abutment portions 14, 15 are bevelled portions located upon the first member engagement component 8 and second member engagement component 9. The bevelled portions 14, 15 of the first member engagement component 8 and the second member engagement component 9 are substantially parallel to one another when in the natural biting position and in the protruding position.

In an alternative embodiment of the engagement arrangement 203 of the mandibular advancement device 1 (as shown in FIGS. 8, 9, 10 and 11) the first member restrictive element 204 and/or second member restrictive element 205 of the articulation restriction arrangement 206 have an indentation 207. The indentation 207 of the first member restrictive element 204 and/or second member restrictive element 205 co-operates with a protruding element 208 of the respective second member restrictive element 205 and/or first member restrictive element 204 of the articulation restriction arrangement 206. This indentation 207 on either or both of the first member restrictive element 204 and second member restrictive element 205 which co-operates with a protruding element 208 of the respective second member restrictive element 205 or first member restrictive element 204 increases the contact area between the first member restrictive element 204 and second member restrictive element 205 when engaged with one another. This improves the efficiency of the device and reduces the stresses and load placed upon the engaging portions of the device resulting in a device which is less likely to fracture and/or break.

The indentation of the first member restrictive element 207a is truncated in a direction opposing an anterior portion of the first member forming a V-shaped indentation. The indentation of the second member restrictive element 207b is truncated in a direction towards an anterior portion of the first member forming a V-shaped indentation.

The protruding element 208 of the articulation arrangement 206 which co-operates with the indentation of the second member restrictive element 207b and/or first member restrictive element 207b corresponds in shape to that of the indention. This corresponding in shape provides a more efficient engagement between the first member 2 and second member 3.

In the alternative the abutment portion 209 of the first member restrictive element 204 and/or the second member restrictive element 205 is configured to form the indentation of the first member restrictive element 207a and/or second member restrictive element 207b of the articulation restriction arrangement 206. Further, the abutment portion 210 of the first member restrictive element 204 and/or the second member restrictive element 205 is configured to form the protruding element 208 of the first member restrictive element 204 and/or second member restrictive element of the articulation restriction means 205.

The first member engagement component 8 and second member engagement component 9 are adjacent one another when the jaw is in its natural biting position and when the jaw is in its predetermined protruding position.

The first member engagement component 8 and second member engagement component 9 are at least partially overlapping when the jaw is in its natural biting position and at least partially overlapping when the jaw is in its protruding position. When in the natural biting position, the longitudinal plane of the first member engagement component 8 is substantially parallel to the longitudinal plane of the second member engagement component 9. When in the protruding position the longitudinal plane of the first member engagement component 8 and the longitudinal plane of the second member engagement component 9 are coincident.

Further, the first member engagement component 8 and second member engagement component 9 are mutually opposing when the jaw is in its natural biting position and when the jaw is in its protruding position. When in the natural biting position and upon movement of the second member 2 from the natural biting position to the protruding position, the second member engagement component 9 is spatially displaced from opposing the first member engagement component 8 along a horizontal plane to opposing the first member engagement component 8 along a substantially vertical plane under the influence of a user moving their lower jaw forward.

The engagement arrangement 4 further comprises braking component 18 to halt the forward sliding movement of the lower jaw of the user (not shown). Advantageously, the braking component 18 signals to the wearer that no further forward movement of the lower jaw (not shown) is necessary to engage the engagement arrangement 4. Once the braking component 18 is reached from the wearer's forward movement of the lower jaw (not shown), to engage with the engagement arrangement 4 the wearer simply slides their lower jaw back in the direction of the natural biting position. Further advantageously, when at sleep an individual's lower jaw can undergo movement whether forward or side to side which can lead to an ineffective engagement or disengagement of the first member 2 and second member 3. Having braking component 18 reduces this risk of disengagement and provides a more effective engagement of the first member 2 and second member 3.

The braking component 18 is a protrusion protruding from a portion of the second member 3 in a direction towards a portion of the first member 2 when in use. The braking component 18 is a ridge, rib or dimple. Alternatively, and as shown in FIG. 3, the braking component 18 is a polygonal shaped protrusion. The braking component 18 of the second member 3 is proximal to an opposing portion 17 of the second member 3 from that of the articulation restriction arrangement 5. The engagement arrangement 4 comprises guide elements 19 to guide the first member engagement component 8 to the second member engagement component 9 for the securement of the second member 3 in the protruding position. The guide element 19 extends between articulation restriction arrangement 5 and the braking component 18; more specifically the guide element 19 extends between second member restrictive element 7 of the articulation restriction arrangement 5 and the braking component 18.

The braking component 18 is configured to interface, interact, interlock and/or otherwise engage with a contact portion 211 of the first member engaging component 8. The contact portion 211 of the first member engaging component is located at a position opposing to that of the first member restrictive element 6.

A portion 212 of the braking component 18 is angled forwards in a direction towards the engagement arrangement 4/203 of the mandibular advancement device 1. The contact portion 211 of the first member engagement component 8 is also an angled portion. The angled portion 212 of the breaking component 18 interacts, abuts and/or otherwise engages with the angled contact portion 211 of the first member engaging component 8.

The angled portion 212 of the braking component 18 and the angled portion 211 of the first member engagement component 8 are substantially parallel to one another when in the natural biting position, in the protruding position and in the braking position.

The braking component 18 acts to prevent the device 1 disengaging in the event that the user inadvertently pushes their jaw forward during sleep. The angled portion 212 of the braking component 18 on the second member 3 and the contact portion 211 of the first member engagement component 8 are angled and inclined at the same or similar angle so that if the user pushes their jaw inadvertently forward an engagement occurs between the braking component 18 and the first member engagement component 8 which makes it difficult for the user to articulate their jaw and as a result the user will relax their lower jaw back into the predetermined protruding position wherein the first member engagement means and second member engagement means are engaged with one another.

Figure 2:
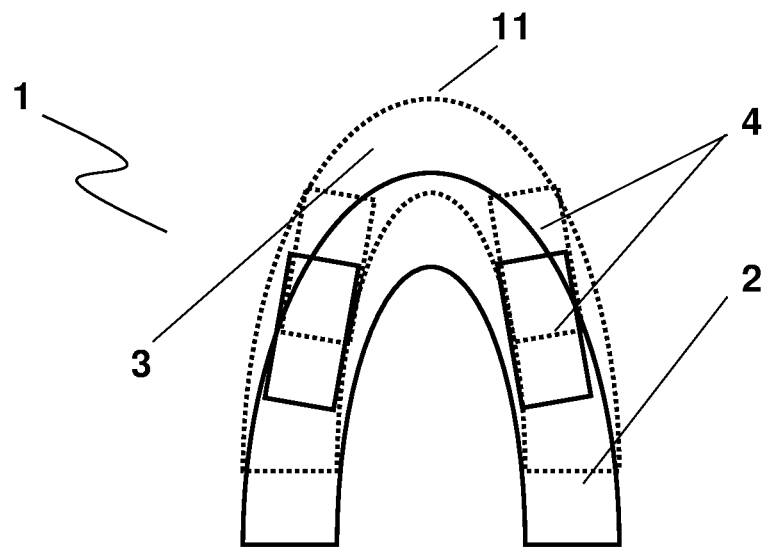
FIG. 2 is a schematic diagram showing the first member and second member of the mandibular advancement kit/device in the lower jaw protruding position.

In use and prior to instances of sleep the user inserts the mandibular advancement device 1 into their mouth such that the first member 2 of fitted substantially over a portion of the teeth of the upper jaw and that the second member 3 is fitted substantially over a portion of the teeth of the lower jaw, the user naturally bites down on the second member 3 placing the jaw into its natural biting position, the user manipulates the lower jaw forward into a protruding position; see FIGS. 1 and 2. In response to this forward movement of the lower jaw by the user the second member 3 slidably moves and the first member engagement component 8 engages a guide element 19 located on the second member 3. Forward movement of the lower jaw continues until the user reaches the braking component 18. Then the user initiates the return of the lower jaw to the natural biting position wherein the first member engagement component 8 is guided by the guide element 19 to the second member engagement component 9 for the securement of the second member 3 in the protruding position and engagement of the articulation restriction arrangement 5.

In relation to the detailed description of the different embodiments of the invention, it will be understood that one or more technical features of one embodiment can be used in combination with one or more technical features of any other embodiment where the transferred use of the one or more technical features would be immediately apparent to a person of ordinary skill in the art to carry out a similar function in a similar way on the other embodiment.

In the preceding discussion of the invention, unless stated to the contrary, the disclosure of alternative values for the upper or lower limit of the permitted range of a parameter, coupled with an indication that one of the said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The features disclosed in the foregoing description or the following drawings, expressed in their specific forms or in terms of a means for performing a disclosed function, or a method or a process of attaining the disclosed result, as appropriate, may separately, or in any combination of such features be utilised for realising the invention in diverse forms thereof.

The invention claimed is:

1. A mandibular advancement device comprising:
a first member, the first member configured to fit substantially over a portion of teeth of the upper jaw of a user, and
a second member, the second member configured to fit substantially over a portion of teeth of the lower jaw of the user, and
an engagement arrangement, configured to be engageable upon a forward manipulation of the lower jaw by the user, to maintain the lower jaw of the user in a predetermined protruding position relative to the upper jaw of the user and the natural biting position of the lower jaw,
wherein the engagement arrangement comprises an articulation restriction arrangement to restrict articulation of the lower jaw of the user when the engagement arrangement is engaged and the lower jaw of the user is in the predetermined protruding position,
wherein the articulation restriction arrangement comprises a first member restrictive element on the first member that protrudes a short distance from a main body of the first member or a main body of the engagement arrangement,
wherein the articulation restriction arrangement comprises a second member restrictive element on the second member that protrudes a short distance from a main body of the second member or a main body of the engagement arrangement,
wherein the first member restrictive element and the second member restrictive element are configured to interface, interact or otherwise engage with one another when the engagement arrangement is engaged to restrict articulation of the lower jaw of the user when in the predetermined protruding position, and
wherein the engagement arrangement further comprises a braking component comprising a protrusion protruding from a portion of the second member towards the first member when in use, the braking component being arranged to halt the forward sliding movement of the lower jaw of the user.

2. The mandibular advancement device as claimed in claim 1, wherein the engagement arrangement comprises first member engagement component and second member engagement component, wherein the first member engagement component protrudes a short distance from the first member in a direction towards the second member when the first member and second member are positioned upon teeth of the upper and lower jaw respectively, and wherein the second member engagement component protrudes a short distance from the second member in a direction towards the first member when the first member and second member are positioned upon teeth of the upper and lower jaw respectively.

3. The mandibular advancement device as claimed in claim 2, wherein the engagement arrangement comprises a guide element located on the second member to guide the first member engagement component to the second member engagement component for the securement of the second member in the protruding position.

4. The mandibular advancement device as claimed in claim 3, wherein the guide element extends between articulation restriction arrangement and the braking component.

5. The mandibular advancement device as claimed in claim 2, wherein the first member engagement component and second member engagement component are configured to be operatively engageable with one another upon forward manipulation of the lower jaw by the user, to maintain the lower jaw of the user in a predetermined protruding position relative to the upper jaw of the user and the natural biting position of the lower jaw.

6. The mandibular advancement device as claimed in claim 2, wherein when in a natural biting position, a first longitudinal plane (L1) of the first member engagement component is parallel to a first longitudinal plane (L1) of the second member engagement component and when in a protruding position a second longitudinal plane (L2) of the first member engagement component and a second longitudinal plane (L2) of the second member engagement component are coincident.

7. The mandibular advancement device as claimed in claim 1, wherein the engagement arrangement is configured to permit lateral movement of the second member when the engagement arrangement is engaged.

8. The mandibular advancement device as claimed in claim 7, wherein the engagement arrangement is configured to permit lateral movement of the second member when the engagement arrangement is engaged between boundary elements.

9. The mandibular advancement device as claimed in claim 8, wherein the boundary elements are positioned and configured to abut or contact at least partially with a portion of the engagement arrangement.

10. The mandibular advancement device as claimed in claim 1, wherein the first member restrictive element or the second member restrictive element of the articulation restriction arrangement comprise an indentation.

11. The mandibular advancement device as claimed in claim 10, wherein the indentation of the first member restrictive element or the second member restrictive element of the articulation restriction arrangement co-operates with a protruding element of the respective second member restrictive element or the first member restrictive element of the articulation restriction arrangement.

12. The mandibular advancement device as claimed in claim 11, wherein the abutment portion of the first member restrictive element is configured to form the indentation of the first member restrictive element or the abutment portion of the second member restrictive element is configured to form the indentation of the second member restrictive element of the articulation restriction arrangement and the abutment portion of the first member restrictive element or the second member restrictive element is configured to form the protruding element of the first member restrictive element or second member restrictive element of the articulation restriction arrangement.

13. The mandibular advancement device as claimed in claim 1, wherein the articulation restriction arrangement comprises a pair of the first member restrictive elements and a pair of the second member restrictive elements.

14. The mandibular advancement device as claimed in claim 13, wherein the pair of first member restrictive elements and second member restrictive elements are located at opposing locations of the first member and second member respectively.

15. The mandibular advancement device as claimed in claim 1, wherein the first member restrictive element and the second member restrictive element of the articulation restriction arrangement comprise abutment portions.

16. The mandibular advancement device as claimed in claim 15, wherein abutment portions of the first member restrictive element and the abutment portions of the second member restrictive element of the articulation restriction arrangement are configured to interface, interact, interlock or otherwise engage with one another.

17. The mandibular advancement device as claimed in claim 1, wherein the second member is moveable relative to the first member under the influence of the user moving their lower jaw forward and backwards to engage the protruding position.

18. The mandibular advancement device as claimed in claim 1, wherein the engagement arrangement is located in an occlusal area where the teeth of the upper jaw would normally contact the teeth of the lower jaw.

19. The mandibular advancement device as claimed in claim 1, wherein the engagement arrangement is located in an anterior portion of the user's mouth when the first member and second member are fitted over a portion of teeth of the upper jaw and lower jaw of the user.

20. The mandibular advancement device as claimed in claim 1, wherein the first member and second member are separate arcuate structures.

21. The mandibular advancement device as claimed in claim 1, wherein the engagement arrangement is configured to releasably engage in use.

22. The mandibular advancement device as claimed in claim 1, wherein the engagement arrangement is configured to enable the articulation restriction arrangement to releasably engage in use.

23. The mandibular advancement device as claimed in claim 1, wherein the first member restrictive element and the second member restrictive element of the articulation restriction arrangement are configured to interface, interact, interlock and/or otherwise engage with one another.

24. The mandibular advancement device as claimed in claim 1, wherein the braking component of the second member is provided on an opposing portion of the second member from that of the articulation restriction arrangement.

25. The mandibular advancement device as claimed in claim 1, wherein the braking component is configured to interface, interlock, interact or otherwise engage with a contact portion of the first member engaging component.

26. A method for adaptively controlling a mandibular advancement device wherein the user's lower jaw is displaced by predetermined increments, the method for adaptively controlling a mandibular advancement device comprising the steps of: fitting a first member substantially over a portion of the teeth of the upper jaw of a user; fitting a second member substantially over a portion of the teeth of the lower jaw of user; engaging an engagement arrangement to maintain the lower jaw of the user in a predetermined protruding position relative to the upper jaw of the user and the natural biting position of the lower jaw; removing the first member substantially over a portion of the teeth of the upper jaw of a user; fitting a second first member substantially over a portion of the teeth of the upper jaw of a user; and engaging a second engagement arrangement to maintain the lower jaw of the user in a predetermined protruding position relative to the upper jaw of the user and the natural biting position of the lower jaw, wherein the first and second engagement arrangements comprise an articulation restriction arrangement to restrict articulation of the lower jaw of the user when the engagement arrangement is engaged and the lower jaw of the user is in the predetermined protruding position, wherein the articulation restriction arrangement comprises a first member restrictive element on the first member that protrudes a short distance from a main body of the first member or a main body of the engagement arrangement, wherein the articulation restriction arrangement comprises a second member restrictive element on the second member that protrudes a short distance from a main body of the second member or a main body of the engagement arrangement, wherein the first member restrictive element and the second member restrictive element are configured to interface, interact or otherwise engage with one another when the engagement arrangement is engaged to restrict articulation of the lower jaw of the user when in the predetermined protruding position, and wherein the engagement arrangement further comprises a braking component comprising a protrusion protruding from a portion of the second member towards the first member when in use, the braking component being arranged to halt the forward sliding movement of the lower jaw of the user.

27. The method as claimed in claim 26, further comprising the steps of: removing the second first member substantially over the portion of the teeth of the upper jaw of a user; fitting a third first member substantially over a portion of the teeth of the upper jaw of a user; and engaging a third engagement arrangement to maintain the lower jaw of the user in a predetermined protruding position relative to the upper jaw of the user and the natural biting position of the lower jaw, wherein the third engagement arrangement comprises an articulation restriction arrangement to restrict articulation of the lower jaw of the user when the engagement arrangement is engaged and the lower jaw of the user is in the predetermined protruding position, wherein the articulation restriction arrangement comprises a first member restrictive element on the first member that protrudes a short distance from a main body of the first member or a main body of the engagement arrangement, wherein the articulation restriction arrangement comprises a second member restrictive element on the second member that protrudes a short distance from a main body of the second member or a main body of the engagement arrangement, wherein the first member restrictive element and the second member restrictive element are configured to interface, interact or otherwise engage with one another when the engagement arrangement is engaged to restrict articulation of the lower jaw of the user when in the predetermined protruding position, and wherein the engagement arrangement further comprises a braking component comprising a protrusion protruding from a portion of the second member towards the first member when in use, the braking component being arranged to halt the forward sliding movement of the lower jaw of the user.

28. A sports mouthguard for optimising breathing input or output of a user by improved airflow, preferably, while comprising:

a first member, the first member configured to fit substantially over a portion of teeth of the upper jaw of a user, and a second member, the second member configured to fit substantially over a portion of teeth of the lower jaw of the user, and an engagement arrangement, the engagement arrangement comprising first member engagement component protruding a short distance from the first member in a direction towards the second member engagement component protruding a short distance from the second member in a direction towards the first member when the first member and second member are positioned upon the teeth of the upper and lower jaw respectively, the first member engagement component and second member engagement component being configured to be operatively engageable with one another upon forward manipulation of the lower jaw by the user, to maintain the lower jaw of the user in a predetermined protruding position relative to the upper jaw of the user and the natural biting position of the lower jaw, wherein the engagement arrangement further comprises an articulation restriction arrangement, the articulation restriction arrangement configured to restrict articulation of the lower jaw of the user when in the predetermined protruding position, wherein the articulation restriction arrangement comprises a first member restrictive element that protrudes a short distance from a main body of the first member or a main body of the engagement arrangement, wherein the articulation restriction arrangement comprises a second member restrictive element that protrudes a short distance from a main body of the second member or a main body of the engagement arrangement, wherein the first member restrictive element and the second member restrictive element are configured to interface, interact or otherwise engage with one another when the engagement arrangement is engaged to restrict articulation of the lower jaw of the user when in the predetermined protruding position, and wherein the engagement arrangement further comprises a braking component comprising a protrusion protruding from a portion of the second member towards the first member when in use, the braking component being arranged to halt the forward sliding movement of the lower jaw of the user.

* * * * *